(12) United States Patent
Yang et al.

(10) Patent No.: US 12,635,978 B2
(45) Date of Patent: May 26, 2026

(54) CART FOR ULTRASONIC IMAGING SYSTEM AND ULTRASONIC IMAGING SYSTEM

(71) Applicant: GE Precision Healthcare LLC, Wauwatosa, WI (US)

(72) Inventors: Zibo Yang, Wuxi (CN); Yalan Yang, Wuxi (CN); Fenggui Huang, Wuxi (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 412 days.

(21) Appl. No.: 18/202,542

(22) Filed: May 26, 2023

(65) Prior Publication Data

US 2023/0380804 A1 Nov. 30, 2023

(30) Foreign Application Priority Data

May 30, 2022 (CN) .......................... 202210598674.0

(51) Int. Cl.
*F16M 11/24* (2006.01)
*A61B 8/00* (2006.01)
*F16M 11/42* (2006.01)

(52) U.S. Cl.
CPC ........... *A61B 8/4405* (2013.01); *F16M 11/24* (2013.01); *F16M 11/42* (2013.01); *F16M 2200/048* (2013.01)

(58) Field of Classification Search
CPC ...... A61B 8/4405; F16M 11/24; F16M 11/42; F16M 2200/048; B62B 2202/56; A61G 2203/20; A47B 9/02; A47B 13/023; A47B 19/06; A47B 2200/0046; A47B 21/02
USPC .......................................................... 280/35
See application file for complete search history.

(56) References Cited

U.S. PATENT DOCUMENTS

| | | | | |
|---|---|---|---|---|
| 8,876,379 B2 * | 11/2014 | DiRisio | ............... | A61B 6/4405 |
| | | | | 378/197 |
| 9,367,061 B2 * | 6/2016 | Miller | ............. | G10K 11/17873 |
| 9,949,561 B2 * | 4/2018 | Aldrich | ................. | A47B 19/06 |
| 10,433,638 B2 * | 10/2019 | Swartz | ................. | F16M 11/42 |
| 10,631,630 B2 * | 4/2020 | Swartz | ................. | F16M 11/42 |
| 10,939,750 B2 * | 3/2021 | Swartz | ................. | A47B 21/06 |
| 10,939,883 B2 * | 3/2021 | Tang | ................. | A61B 6/4458 |
| 11,311,102 B2 * | 4/2022 | Swartz | ............... | F16M 11/046 |
| 11,771,386 B2 * | 10/2023 | Tang | ................. | A61B 6/4458 |
| | | | | 378/198 |
| 2013/0146728 A1 * | 6/2013 | Ergun | ................. | A47B 21/02 |
| | | | | 248/299.1 |

(Continued)

*Primary Examiner* — James A Shriver, II
*Assistant Examiner* — Hilary L Johns

(57) ABSTRACT

Provided in the present invention are a cart for an ultrasonic imaging system and an ultrasonic imaging system. The cart includes a height adjustable column, and the column includes an elevation device and a balancing unit adjustment device. The elevation device is used to adjust the height of the cart, and the balancing unit adjustment device includes a force balancing unit and a knob. The force balancing unit includes an elastic assembly, and the force balancing unit is used to balance the lifting force required by the elevation device to implement lifting. The knob is connected to the force balancing unit and installed on the outside of the column to adjust the elasticity of the elastic assembly, so as to alter the lifting force.

18 Claims, 7 Drawing Sheets

(56)     References Cited

U.S. PATENT DOCUMENTS

| | | | |
|---|---|---|---|
| 2015/0223890 A1* | 8/2015 | Miller | A61B 50/10 |
| | | | 726/17 |
| 2015/0223891 A1* | 8/2015 | Miller | A61B 50/15 |
| | | | 726/19 |
| 2015/0223892 A1* | 8/2015 | Miller | A61B 50/18 |
| | | | 345/174 |
| 2015/0227127 A1* | 8/2015 | Miller | G16H 20/13 |
| | | | 700/244 |
| 2016/0073772 A1* | 3/2016 | Ergun | A47B 21/03 |
| | | | 108/28 |
| 2016/0270525 A1* | 9/2016 | Aldrich | H01F 7/0205 |
| 2017/0027541 A1* | 2/2017 | Henderson | A61B 8/4405 |
| 2018/0168334 A1* | 6/2018 | Swartz | F16M 11/046 |
| 2019/0350357 A1* | 11/2019 | Swartz | A47B 21/06 |
| 2020/0138184 A1* | 5/2020 | Swartz | A47B 21/02 |
| 2020/0187885 A1* | 6/2020 | Tang | A61B 6/447 |
| 2021/0161288 A1* | 6/2021 | Swartz | F16M 13/00 |

* cited by examiner

CART FOR ULTRASONIC IMAGING SYSTEM AND ULTRASONIC IMAGING SYSTEM

CROSS-REFERENCE TO RELATED APPLICATION

This application claims priority to Chinese patent application number 202210598674.0, filed on May 30, 2022, the entirety of which is incorporated herein by reference.

TECHNICAL FIELD

The present invention relates to the field of ultrasonic examination, and in particular to a cart for an ultrasonic imaging system and an ultrasonic imaging system.

BACKGROUND

Ultrasound imaging is a medical imaging technique for imaging organs and soft tissues in the human body. Ultrasonic imaging uses real-time and non-invasive high-frequency sound waves to produce two-dimensional (2 D) images, three-dimensional (3 D) images, and/or four-dimensional (4 D) images (i.e., real-time/continuous 3 D images).

The cart for an ultrasonic imaging system is usually height adjustable, and often requires multiple external accessories on the cart. For example, one or more of accessories such as a multi-probe port, a printer, a partition plate, and a storage basket can be installed on the cart to balance the downward pressing and/or upward driving force needed to adjust the height of the cart. However, the user is not in need of these accessories in all cases. If these accessories are not installed, the downward pressing and/or upward driving force needed when adjusting the height of the cart will be relatively large. Therefore, a larger force is required to achieve such height adjustment, and thus, the user experience is poor.

SUMMARY

The present invention provides a cart for an ultrasonic imaging system and an ultrasonic imaging system.

Illustrative embodiments of the present invention provide a cart for an ultrasonic imaging system, said cart comprising a height adjustable column, and said column comprising an elevation device and a balancing unit adjustment device. Said elevation device is used to adjust the height of said cart, and said balancing unit adjustment device comprises a force balancing unit. Said force balancing unit comprises an elastic assembly and said force balancing unit is used to balance the lifting force required by said elevation device to implement lifting.

Illustrative embodiments of the present invention further provide an ultrasonic imaging system comprising a height adjustable cart, said cart comprising an elevation device and a balancing unit adjustment device. Said elevation device is used to adjust the height of said cart, and said balancing unit adjustment device comprises a force balancing unit. Said force balancing unit comprises an elastic assembly and said force balancing unit is used to balance the lifting force required by said elevation device to implement lifting.

Other features and aspects will become apparent from the following detailed description, accompanying drawings, and claims.

BRIEF DESCRIPTION OF THE DRAWINGS

The present invention can be better understood through the description of exemplary embodiments of the present invention in conjunction with the accompanying drawings, in which.

DETAILED DESCRIPTION

Specific embodiments of the present invention will be described below. It should be noted that in the specific description of these embodiments, for the sake of brevity and conciseness, this specification may not describe all features of the actual embodiments in detail. It should be understood that in the actual implementation process of any embodiments, just as in the process of any engineering project or design project, a variety of specific decisions are often made to achieve specific goals of the developer and to meet system-related or business-related constraints, which may also vary from one embodiments to another. Furthermore, it should also be understood that although efforts made in such development processes may be complex and tedious, for those of ordinary skill in the art related to the content disclosed in the present invention, some design, manufacture, or production changes based on the technical content disclosed in the present disclosure are only common technical means and should not be construed as insufficient content of the present disclosure.

Unless defined otherwise, technical terms or scientific terms used in the claims and specification should have usual meanings understood by those of ordinary skill in the technical field to which the present invention belongs. The terms "first," "second" and similar terms used in the description and claims of the patent application of the present invention do not denote any order, quantity, or importance, but are merely intended to distinguish between different constituents. The terms "one" or "a/an" and similar terms do not denote a limitation of quantity, but rather the presence of at least one. The terms "include" or "comprise" and similar terms mean that an element or article preceding the term "include" or "comprise" encompasses elements or articles listed after "include" or "comprise," and does not exclude other elements or articles. The terms "connect" or "connected" and similar words are not limited to physical or mechanical connections, and are not limited to direct or indirect connections.

Figure 1:
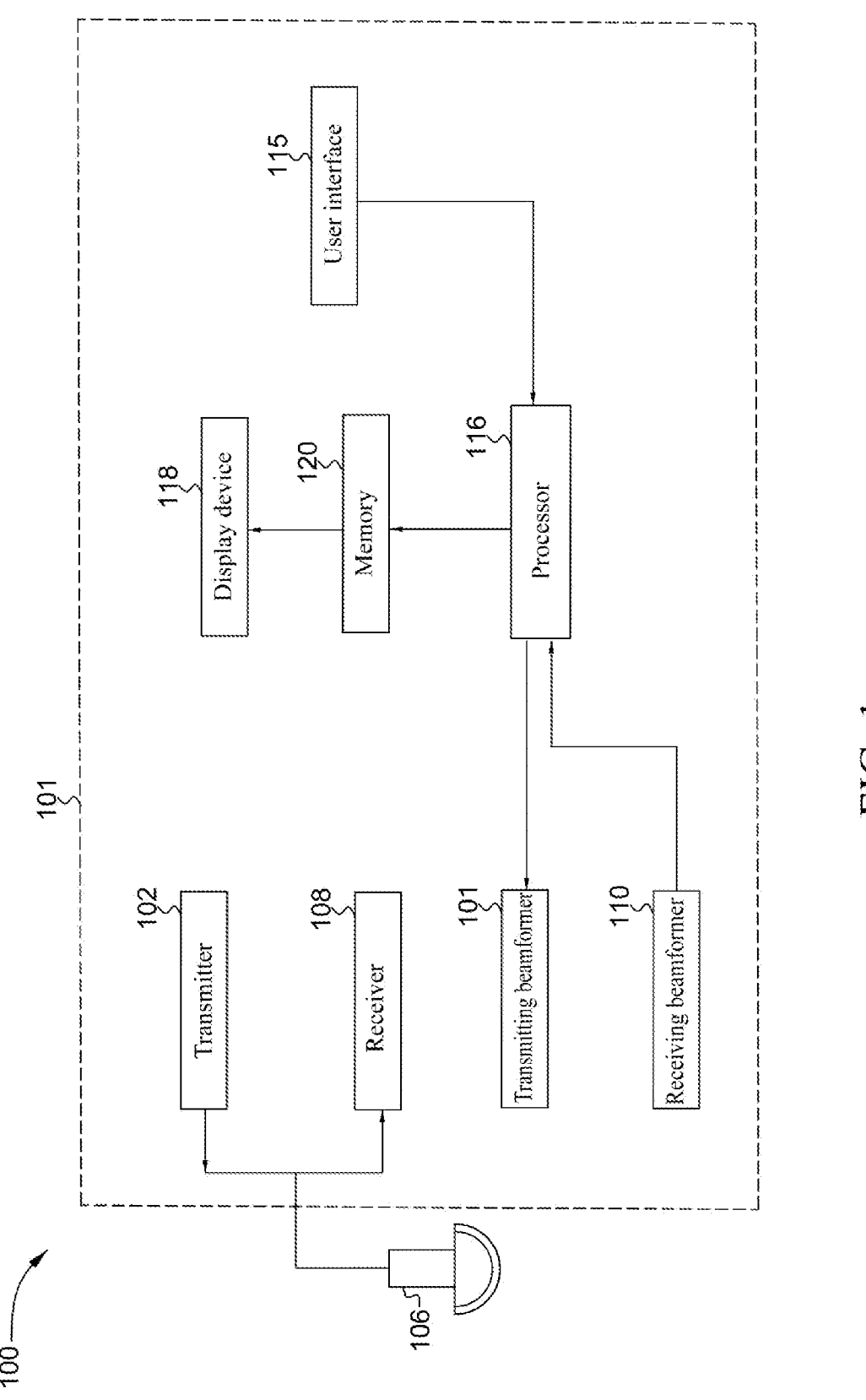
FIG. 1 is a schematic diagram of an ultrasound imaging system according to some embodiments of the present invention.

FIG. 1 shows an ultrasound imaging system 100 according to some embodiments of the present invention. As shown in the figure, the ultrasonic imaging system 100 includes a transmitting beamformer 101 and a transmitter 102, which drive elements 104 within a probe 106 to transmit ultrasonic pulse signals into the body (not shown). According to various embodiments, the probe 106 may be any type of probe including a linear probe, a curved array probe, a 1.25 D array probe, a 1.5 D array probe, a 1.75 D array probe, or a 2 D array probe. According to other embodiments, the probe 106 may also be a mechanical probe, for example, a mechanical 4 D probe or a hybrid probe. The probe 106 may be configured to acquire 4 D ultrasonic data, and the 4 D ultrasonic data includes information related to how volume changes over time. Each volume may include a plurality of 2 D images or slices. Still referring to FIG. 1, the ultrasonic pulse signals are backscattered from structures in the body (e.g., blood cells or muscle tissue) to produce echoes that return to the elements 104. The echoes are converted by the elements 104 into electrical signals or ultrasonic data, and the electrical signals are received by a receiver 108. The electrical signals representing the received echoes pass through a receiving beamformer 110 that outputs ultrasonic data. According to some embodiments, the probe 106 may include an electronic circuit to perform all of or part of transmitting beamforming and/or receiving beamforming. For example, all or part of the transmitting beamformer 101, the transmitter 102, the receiver 108, and the receiving beamformer 110 may be located in the probe 106.

The term "scan" or "scanning" may also be used in the present disclosure to refer to acquiring data through the process of transmitting and receiving ultrasonic signals. The terms "data" and "ultrasonic data" may be used in the present disclosure to refer to one or a plurality of datasets acquired using the ultrasonic imaging system. A user interface 115 may be configured to control operation of the ultrasonic imaging system 100. The user interface may be configured to control input of patient data, or select various modes, operations, parameters, and so on. The user interface 115 may include one or more input devices, such as a keyboard, touch screen, trackball, or any other user input apparatuses.

The ultrasonic imaging system 100 further includes a processor 116, which controls the transmitting beamformer 101, the transmitter 102, the receiver 108, and the receiving beamformer 110. According to various embodiments, the receiving beamformer 110 may be a conventional hardware beamformer or software beamformer. If the receiving beamformer 110 is a software beamformer, then the receiving beamformer may include one or a plurality of the following components: a graphics processing unit (GPU), a microprocessor, a central processing unit (CPU), a digital signal processor (DSP), or any other type of processor capable of performing logical operations. The beamformer 110 may be configured to implement conventional beamforming techniques and techniques such as retrospective transmit beamforming (RTB).

The processor 116 is in electronic communication with the probe 106. The processor 116 may control the probe 106 to acquire ultrasonic data. The processor 116 controls which elements 104 are activated and the shape of a beam transmitted from the probe 106. The processor 116 is further in electronic communication with a display apparatus 118, and the processor 116 may process the ultrasonic data into an image for display on the display apparatus 118. For the purpose of the present disclosure, the term "electronic communication" may be defined to include wired connection and wireless connection.

According to an embodiment, the processor 116 may include a central processing unit (CPU). According to other embodiments, the processor 116 may include other electronic components capable of performing processing functions, for example, a digital signal processor, a field-programmable gate array (FPGA), a graphics processing unit (GPU), or any other type of processor. According to other embodiments, the processor 116 may include a plurality of electronic components capable of performing processing functions. For example, the processor 116 may include two or more electronic components selected from a list including the following electronic components: a central processing unit (CPU), a digital signal processor (DSP), a field-programmable gate array (FPGA), and a graphics processing unit (GPU). According to another embodiment, the processor 116 may include a complex demodulator (not shown), which demodulates RF data and generates raw data.

In another embodiment, the demodulation may be performed earlier in the processing chain. The processor 116 may be adapted to perform one or a plurality of processing operations on data according to a plurality of selectable ultrasound modalities. As echo signals are received, data may be processed in real time in a scanning stage. For the purpose of the present disclosure, the term "real time" is defined to include a process that is performed without any intentional delay. The real-time frame or volume rate may vary on the basis of the site where data is acquired or the size of the volume and specific parameters used in the acquisition process. The data may be temporarily stored in a buffer (not shown) in the scanning stage and processed in a less real-time manner in live or offline operations. Some embodiments of the present application may include a plurality of processors (not shown) to cope with processing tasks. For example, a first processor may be configured to demodulate and decimate RF signals, while a second processor may be configured to further process data which is then displayed as an image. It should be recognized that other embodiments may use different processor arrangements. For embodiments where the receiving beamformer 110 is a software beamformer, the aforementioned processing tasks belonging to the processor 116 and the software beamformer herein may be performed by a single processor, for example, the receiving beamformer 110 or the processor 116. Alternatively, the processing functions belonging to the processor 116 and the software beamformer may be distributed among any number of separate processing components in a different manner.

According to an embodiment, the ultrasonic imaging system 100 may continuously acquire ultrasonic data at a frame rate of, for example, 10 Hz to 30 Hz. An image generated from the data may be refreshed at a similar frame rate. Data may be acquired and displayed at different rates in other embodiments. For example, depending on the size of the volume and potential applications, ultrasonic data may be acquired at a frame rate of less than 10 Hz or greater than 30 Hz in some embodiments. For example, many applications involve acquiring ultrasonic data at a frame rate of 50 Hz. A memory 120 is included therein to store processing frames for acquiring data. In an exemplary embodiment, the memory 120 has sufficient capacity to store ultrasonic data frames which are acquired over a period of time and are at least a few seconds long. The data frames are stored in a manner that facilitates retrieval according to the order or time of acquisition thereof. The memory 120 may include any known data storage medium.

In various embodiments of the present application, data may be processed by the processor 116 by means of modules of other or different related modes (e.g., B-mode, color Doppler, M-mode, color M-mode, spectral Doppler, elastography, TVI, strain, strain rate, etc.) to form 2 D or 3 D images. For example, one or a plurality of modules may generate B-mode, color Doppler, M-mode, color M-mode, spectral Doppler, elastography, TVI, strain, strain rate, a combination thereof, etc. Image bundles and/or frames are stored, and timing information indicating the time when data is acquired in the memory may be recorded. The module may include, for example, a scan conversion module that performs scan conversion operations to convert image frames from a coordinate bundle space to display space coordinates. A video processor module may be provided that reads image frames from the memory and displays the image frames in real time while performing operation on a patient. The video processor module may store image frames in an image memory, read images from the image memory, and display the images. The ultrasonic imaging system 100 may be a console-based system, a laptop computer, a handheld or portable system, or any other configuration.

Figure 2:
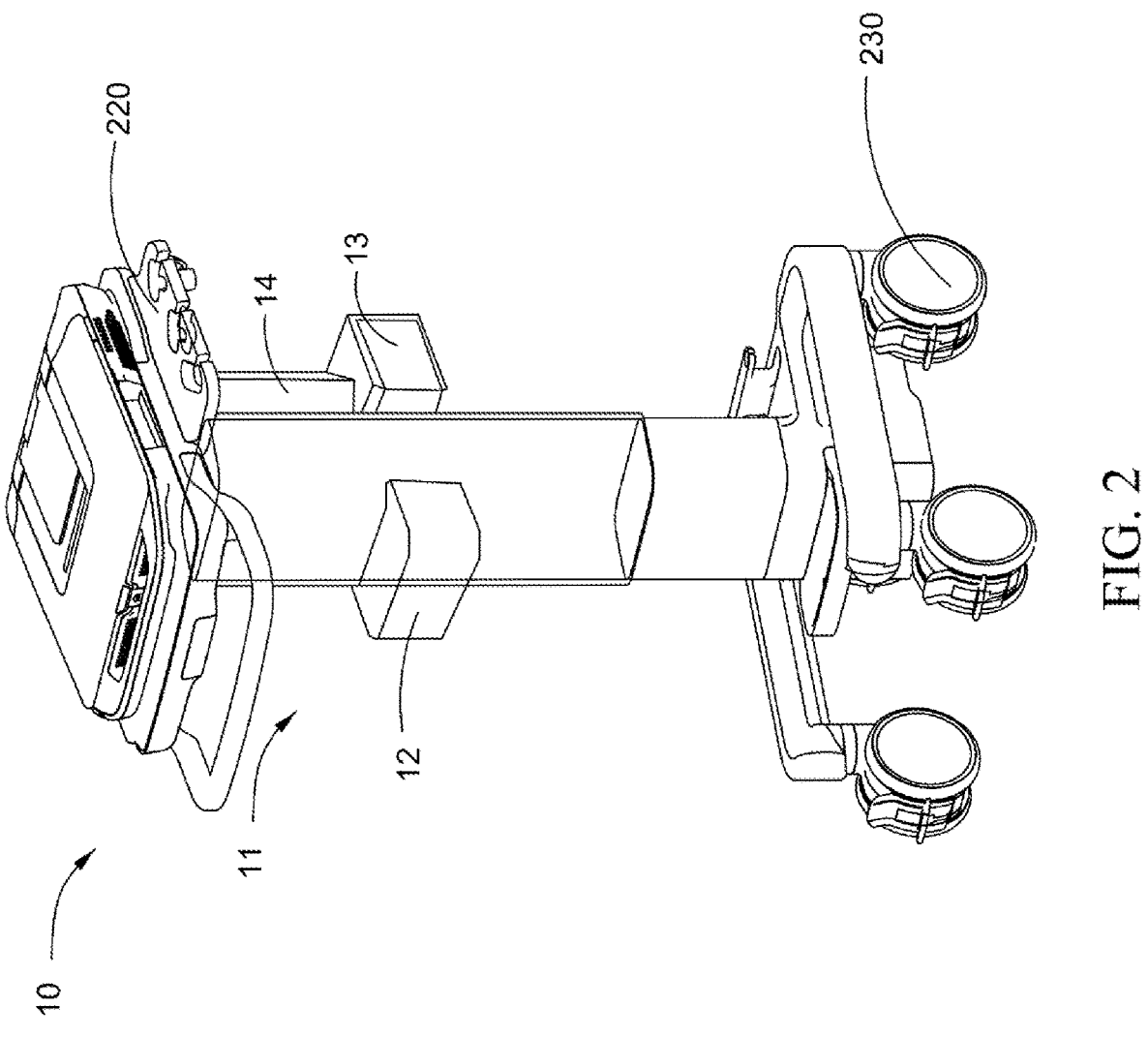
FIG. 2 is a schematic diagram of a cart in a prior art ultrasonic imaging system.

FIG. 2 illustrates a schematic diagram of a cart of a prior art ultrasonic imaging system. As shown in FIG. 2, the ultrasonic imaging system 10 includes a cart 11 that includes one or more recesses or tracks on the outside of a column of the cart. One or more accessories are installed on the column. The accessories include a storage basket 12, a shelf 13 and/or a multi-probe port 14. The storage basket can be used to hold sterilization reagents, etc., and the shelf can be used to hold tools such as a printer. The multi-probe port includes a plurality of ports that can hold ultrasound probes. The one or more accessories have a weight to balance or counterweight the downward pressing force and/or upward driving force required during the height adjustment process. However, the pressing force or driving force required by the elevation device are different according to different system configurations. However, the balancing force or counterweight provided by these accessories is constant. Therefore, the height adjustment of the cart is not smooth during the actual height adjustment process, and multiple accessories will increase the weight of the ultrasonic imaging system as a whole. Furthermore, the user is not in need of these accessories in all cases. If these accessories are not installed, the downward pressing force and/or upward driving force required during the height adjustment of the cart is relatively large. Therefore, a larger force is required to achieve such height adjustment, and thus, the user experience is poor.

Therefore, in order to better facilitate the height adjustment of the cart without requiring the user to purchase or install additional accessories, the present invention proposes a cart that can be controlled by the user in terms of the amount of lifting force used, as well as an ultrasonic imaging system.

Figure 3:
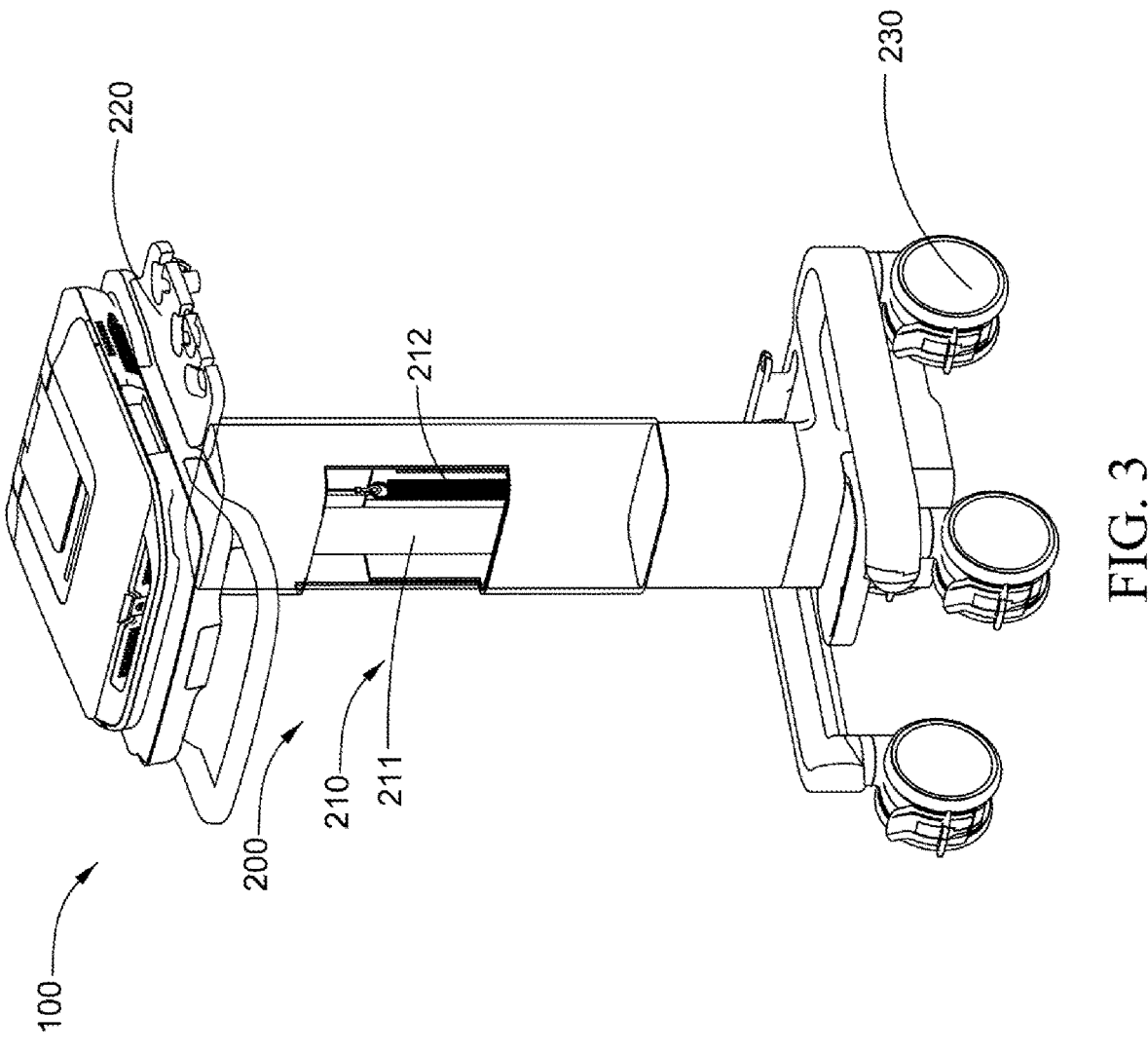
FIG. 3 is a schematic diagram of a cart in an ultrasonic imaging system according to some embodiments of the present invention.
Figure 4:
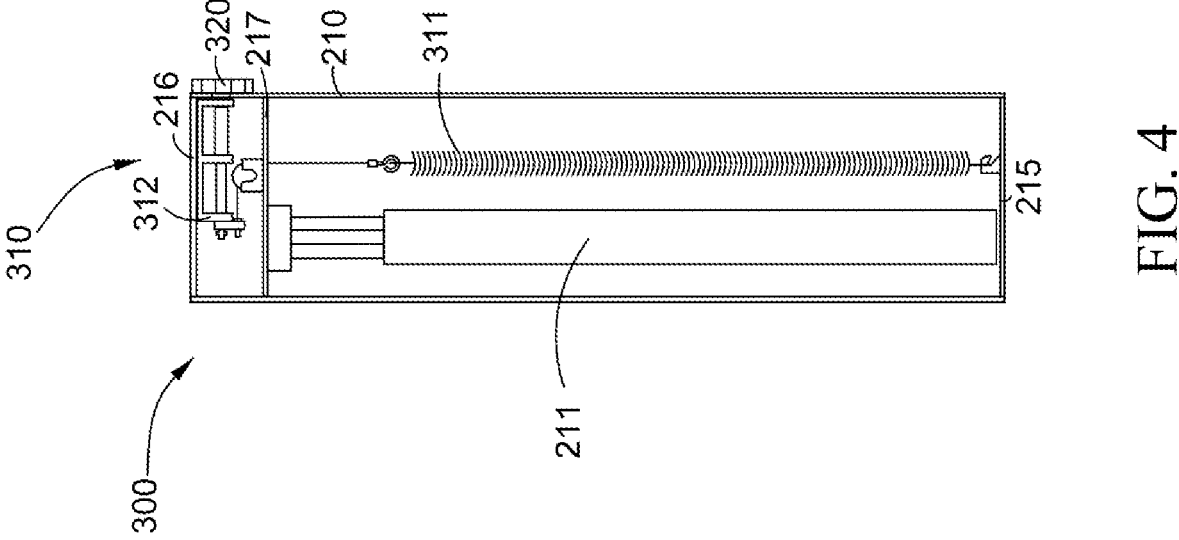
FIG. 4 is a schematic diagram of a balancing unit adjustment device in the cart shown in FIG. 3 in accordance with an embodiment.

FIG. 3 illustrates a schematic view of a cart of an ultrasonic imaging system according to some embodiments of the present invention, and FIG. 4 illustrates a schematic view of a balancing unit adjustment device in the cart shown in FIG. 3. Although FIG. 3 illustrates a convenient ultrasonic imaging system, it should be understood by those of ordinary skills in the art that the cart of the present invention can be used for any ultrasonic imaging systems and is not limited to the type as shown in FIG. 3.

As shown in FIGS. 3 to 4, the ultrasonic imaging system 100 includes a cart 200. The cart 200 includes a column 210, a carrier section 220, and a mobile section 230. The column 210 is connected between the carrier section 220 and the mobile section 230. The carrier section 220 is used to hold or carry the ultrasound main unit and/or other devices, and the mobile section 230 includes a plurality of casters for moving the ultrasonic imaging system.

The ultrasound main unit can be placed on the top of the cart and electrically connected to the electrical connector on the cart. The ultrasound main unit may include a primary battery pack. The cart may include a power supply box, one end of which may be connected to an external input of AC power and the other end may be connected to a backup power supply unit. The cart can be used to carry the ultrasound main unit and the backup power supply unit.

Specifically, the column 210 is height adjustable, and the column 210 includes an upper casing and a lower casing, the upper casing and lower casing being nested together to form a nested structure, and the upper casing can move relative to the lower casing, thereby achieving height adjustment. The height of the column 210 can be adjusted, so that the carrier section 220 or cart 200 can be adjusted to different heights, which can simultaneously meet the different height requirements of the cart as required by different doctors and in different locations. The casing of the column may include one or more slots or grooves for attaching one or more accessories, e.g., probe ports, etc.

In some embodiments, the column 210 includes an elevation device 211 and a balancing unit adjustment device 212. The elevation device 211 is used for adjusting the height of the cart and the balancing unit adjustment device 212 is used for adjusting or altering the lifting force required by the column 210 or cart 200 during the height adjustment process. In some non-limiting embodiments, the elevation device 211 includes a gas spring structure.

In some embodiments, the height adjustment of the column of the ultrasonic imaging system is manually controlled. The height adjustment of the column requires manual control by the user, and the above "lifting force" can refer to the upward driving force needed to achieve a lifting process of the column and/or the downward pressing force needed to achieve a lowering process of the column. For example, the user can apply a pressing force to the carrier section, which causes the upper casing of the column to move downward relative to the lower casing, which causes the cart to descend, or the user can lift the carrier section, which causes the upper casing of the column to move upward relative to the lower casing, which causes the cart to ascend, and such force required by the user is the lifting force.

The column 210 includes a base plate 215, a top plate 216, and a partition plate 217 arranged adjacent to the top plate 216, and a space is formed between the partition plate 217 and the top plate 216. The elevation device 211 is arranged between the base plate 215 and the partition plate 217, and one end of the elastic assembly 311 is fixed to the base plate 215. Specifically, the base plate 215 is the part connected to the mobile section 230 and the top plate 216 is the part connected to the carrier section 220. Specifically, a first space is formed between the base plate 215 and the partition plate 217, and a second space is formed between the top plate 215 and the partition plate 217. The size of the first space is larger than the size of the second space, and the elevation device, for example, the gas spring structure is located in the first space.

In some embodiments, the elevation device 211 and the balancing unit adjustment device 212 are arranged in parallel in the column 210, and the balancing unit adjustment device 212 can adjust or alter the lifting force, i.e., the upward driving force and downward pressing force required by the user to adjust the height of the column. Specifically, for a certain elevation device, the upward driving force and downward pressing force required for height adjustment is fixed. By setting up a balancing unit adjustment device in the column, the upward driving force and downward pressing force required by the user to adjust the height of the column can be deceased or reduced, which is easy to control and can easily meet the needs of different heights and different scenarios of applications, so as to improve the user experience. The sleeve type column design has a relatively large contact area, which enables the height adjustment by the elevation device and balancing unit adjustment device (or elastic assembly) installed therein, without causing such height adjustment to be difficult or rough due to unbalanced forces.

In some embodiments, the balancing unit adjustment device 300/212 includes a force balancing unit 310. The force balancing unit 310 includes an elastic assembly 311, and the force balancing unit 310 is used to balance the lifting force required to achieve height adjustment of the column 210. In some non-limiting embodiments, the elastic assembly includes a tension spring, and different tension states of the tension spring are capable of producing different amounts of elasticity.

In some embodiments, the balancing unit adjustment device 300/212 further includes a knob 320. The knob 320 is connected to the force balancing unit 310 and is installed on the outside of the column 210 to adjust the elasticity of the elastic assembly 311, thereby altering the lifting force.

By arranging the knob 320 on the outside of the column, it is easy for a user to operate, and by arranging the knob 320, the elasticity of the elastic assembly is adjustable, so that the force required by the elevation device to adjust the height is adjustable, and the user can adjust on their own to meet different application scenario requirements or needs. For example, some users want to adjust the height with a greater force for a small range of precise adjustment, and some users want to use less force to adjust the height, and the different needs of different users can be met, thereby improving the user experience.

In some embodiments, the force balancing unit 310 includes an adjustment assembly 312. The adjustment assembly 312 is arranged in the space between the partition plate 217 and the top plate 216 (specifically, in the second space) and is connected to the knob 320. One end of the elastic assembly 311 is fixed to the base plate 215, the other end is fixed to the adjustment assembly 312, and the adjustment assembly 312 can displace the elastic assembly 311 to alter the elasticity of the elastic assembly 311.

Specifically, when the knob 320 is rotated, the adjustment assembly 312 is displaced, which in turn drives the elastic assembly 311 to be displaced, which in turn alters the elasticity of the elastic assembly 311 to adjust the upward driving force and/or downward pressing force of the elevation device.

Figure 5:
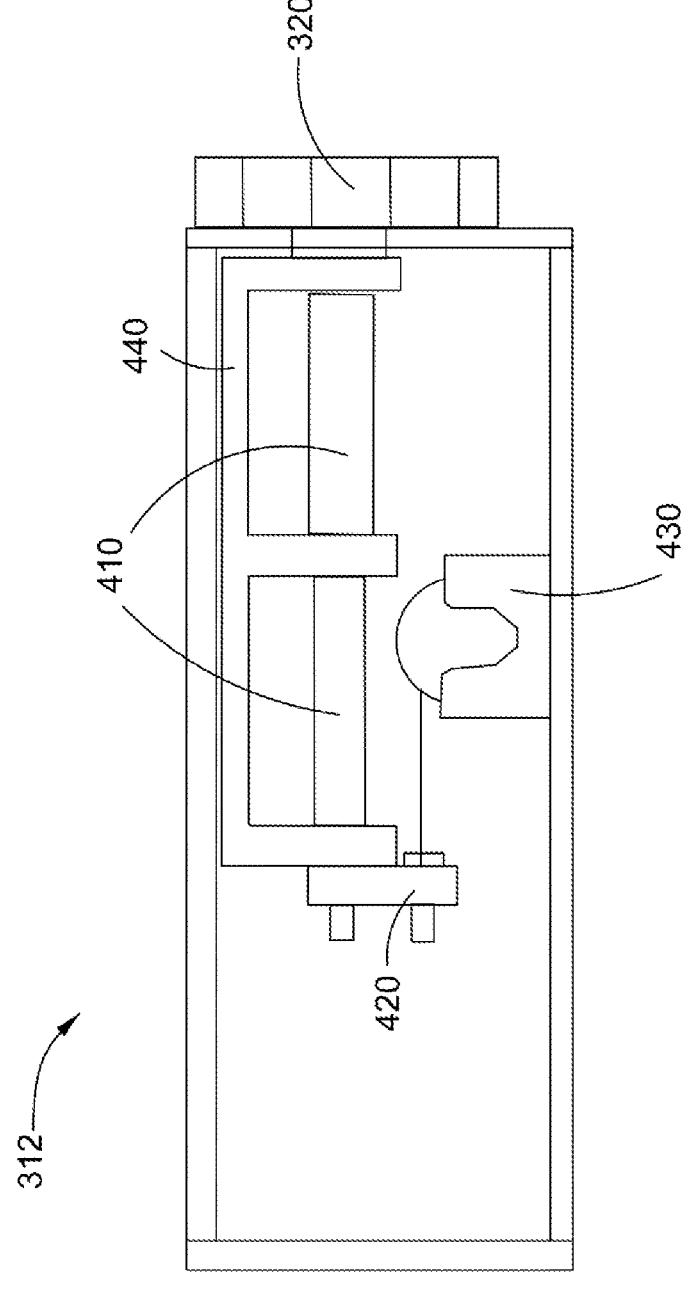
FIG. 5 is a schematic diagram illustrating that an adjustment assembly of the balancing unit adjustment device shown in FIG. 4 is in a first position in accordance with an embodiment.
Figure 6:
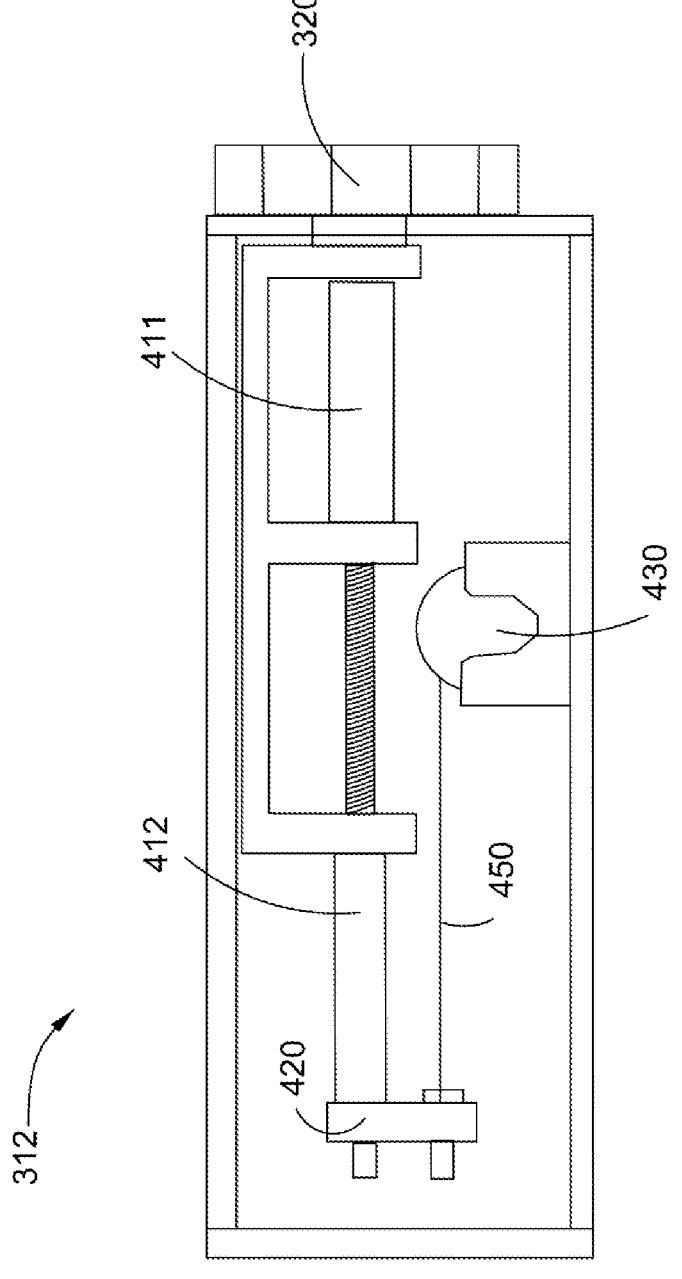
FIG. 6 is a schematic diagram illustrating that the adjustment assembly of the balancing unit adjustment device shown in FIG. 4 is in a second position in accordance with an embodiment.
Figure 7:
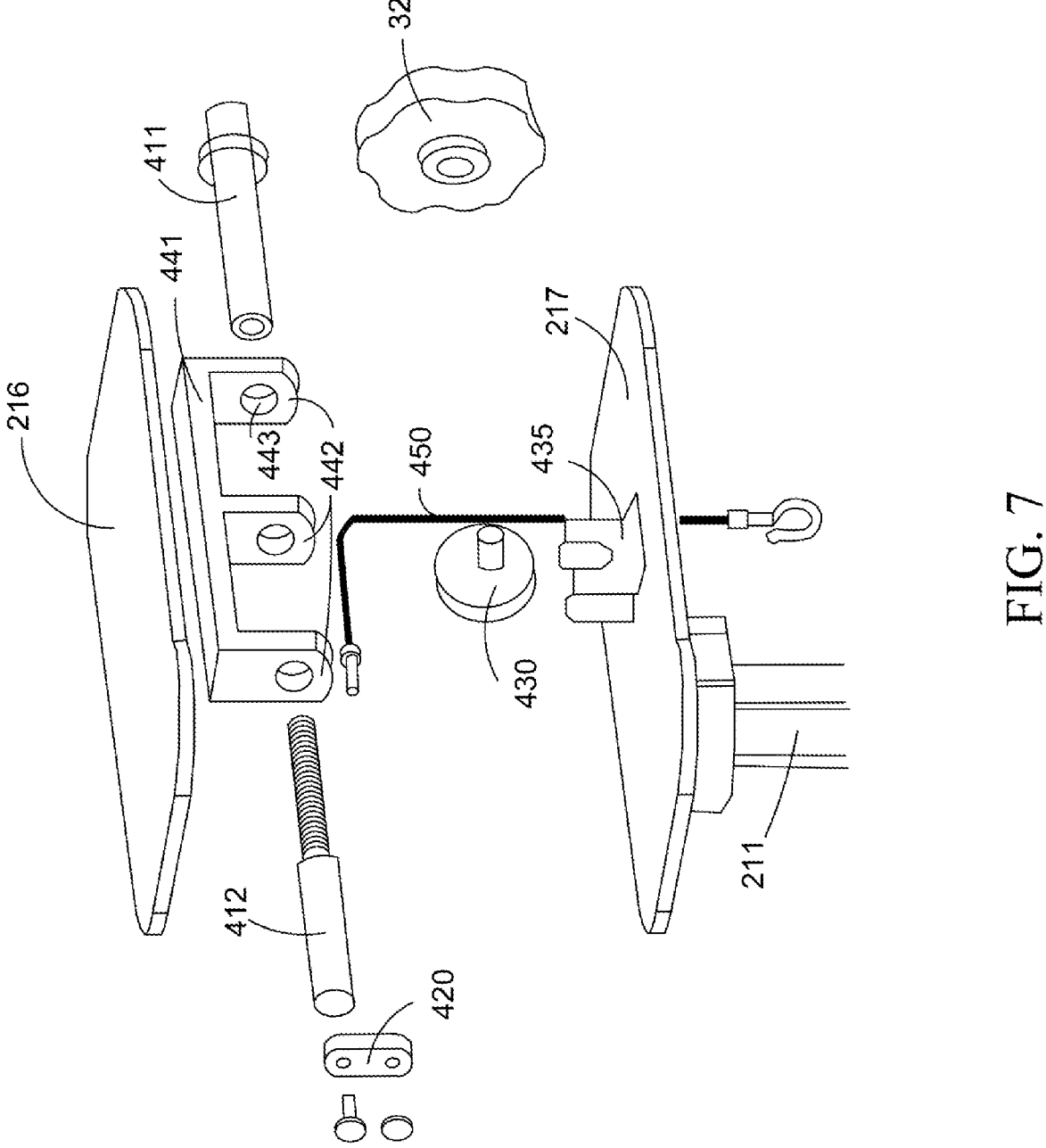
FIG. 7 is an exploded view of the adjustment assembly in the balancing unit adjustment device shown in FIG. 4 in accordance with an embodiment.

FIG. 5 illustrates a schematic view of the adjustment assembly 312 in a first position, and FIG. 6 illustrates a schematic view of the adjustment assembly 312 in a second position, while FIG. 7 illustrates an exploded view of the adjustment assembly 312. As shown in FIGS. 5 to 7, the adjustment assembly 312 includes a screw nut 410, a connection member 420, and a roller 430.

Specifically, one end of the screw nut 410 is connected to the knob 320 and is capable of moving in a first direction under the control of the knob 320, wherein the first direction is perpendicular to the direction of rotation of the knob 320. The screw nut 410 includes a nut portion 411 and a screw portion 412, and the nut portion 411 is connected to the knob 320 and the screw portion 412 is connected to the connection member 420. The screw portion 412 can be screwed in or out from the nut portion. The inner side of the nut portion 411 contains threads, and the threads of the nut portion 411 and the screw portion 412 are matched so that the screw portion 412 can move linearly along the nut portion 411 when the nut portion 411 is rotated, and the connection member 420 linked thereto also moves linearly.

The connection member 420 is connected to the other end of the screw nut 410. Specifically, the connection member 420 is fixed to the end of the screw portion 412. In some embodiments, the connection member 420 includes two through-holes, one of which is used to secure the screw portion 412 of the screw nut 410 and the other is used to secure a connection wire 450 connected to the elastic assembly 311. One end of the connection wire 450 is fixed to the connection member 420, and the other end is fixed to the elastic assembly 311. Specifically, the connection member 420 and the screw portion 412 of the screw nut 410 are rigidly connected.

The roller 430 is fixed to the partition plate 217 and the other end of the elastic assembly 311 is fixed to the connection member 420 via the connection wire 450, passing through the roller 430. Specifically, the roller 430 is secured to the partition plate 217 by a roller bracket 435, and the roller bracket 435 is provided with a recess for securing the roller 430. Specifically, one end of the connection wire 450 is fixed to the connection member 420 and the other end is fixed to the elastic assembly 311. The length of the connection wire 450 is fixed so that when the connection member 420 is displaced, the connection wire 450 can drive the elastic assembly 311 to be displaced.

In some embodiments, the adjustment assembly 312 further includes a support frame 440, the support frame 440 including a body 441 secured to the top plate 216, and a plurality of extensions 442 extending along the body 441 toward the direction of the partition plate 217, and the plurality of extensions 442 including through-holes 443 respectively provided in the first direction, and the screw nut 440 is installed along the plurality of through-holes 443. Specifically, the support frame 440 includes three extensions. For example, a first extension, a second extension, and a third extension provided in sequence from the direction adjacent to the knob to the direction away from the knob, and a first through-hole, a second through-hole, and a third through-hole are provided therein, respectively. The nut portion of the screw nut is provided substantially between the first through-hole and the second through-hole, and the screw portion is provided between the second through-hole and the third through-hole when the screw portion is fully screwed into the nut portion.

By arranging an adjustment assembly at one end of the elastic assembly, e.g., in a manner of cooperation between a screw nut, a connection member and a knob, the spring tension is adjusted by means of a knob with such adjustment method, making it possible to tighten the spring without easily retracting, which is safe and reliable.

With reference to the first position as described in FIG. 5 and the second position as described in FIG. 6, when the adjustment assembly 312 is in the first position, and when the knob 320 is adjusted (e.g., clockwise rotation), the screw portion 412 in the screw nut 410 is screwed out of the nut portion 411, which in turn drives the connection member 420 which is rigidly connected to the screw portion 412 to move in the first direction toward the direction away from the knob 320, which in turn causes the connection wire 450 which is connected to the connection member 420 to displace, so that the elastic assembly (tension spring) is stretched, thereby increasing the elastic force of the elastic assembly, and in turn the balancing lifting force used by the elevation device for the height adjustment is reduced. That is, the user needs less force to achieve the height adjustment of the cart or column.

When the adjustment assembly 312 is in the second position, the lifting force required to achieve the height adjustment by the elevation device is minimized at this point. When the knob is adjusted in the opposite direction (e.g., anti-clockwise), the screw portion 412 in the screw nut 410 is gradually screwed into the nut portion 411, which in turn drives the connection member 420 which is rigidly connected to the screw portion 412 to move in the first direction toward the direction adjacent to the knob 320, which in turn makes the connection wire 450 which is connected to the connection member 420 to displace, thereby causing the elastic assembly (tension spring) to change from a stretched or tensioned state to a rebounded state, which reduces the elasticity of the elastic assembly, and in turn the balancing lifting force used by the elevation device for the height adjustment is increased.

Specifically, assuming that F is the force required by the user to adjust the height of the cart, and $F_1$ is the force required to adjust the height by the elevation device, when there is no balancing unit adjustment device, $F=F_1$, and when the balancing unit adjustment device is added, the force balanced by the balancing unit adjustment device is $F_2$, where $F_2=kx$, k being the coefficient of the tension spring, and x being the distance of the tension spring displacement or stretch, and at this point, $F=F_1-F_2$. Therefore, the greater the magnitude x of the tension spring displacement or stretch is, the greater $F_2$ is, and the smaller the force F required by the user becomes.

In some non-limiting embodiments, for the cart in the present invention including the balancing unit adjustment device, one or more accessories can also be installed on the column. In the process of adjusting the height of the cart, if the user feels that such height adjustment is difficult or not smooth, the knob can also be adjusted to enable the force balancing unit to adjust the elasticity of the elastic assembly to further alter the lifting force required to achieve the height adjustment by the elevation device. Secondly, when the user needs a small range of precise height adjustment in the process of the height adjustment, the user can also adjust the knob in the opposite direction to reduce the elasticity of the elastic assembly, so as to increase the lifting force required to achieve the height adjustment by the elevation device.

In the ultrasonic imaging system and the cart used for such system proposed in the present invention, by adding a balancing unit adjustment device in addition to the elevation device, it is possible not to necessarily or forcibly install additional attachments or accessories on the cart, and the force required by the user to adjust the height of the cart can be reduced. Furthermore, by arranging a knob on the outside of the column of the cart and arranging an adjustment assembly, the user can adjust the balancing force generated by the balancing unit according to their own needs or requirements, which can meet the needs of different scenarios, and enhance the user experience.

Some embodiments of the present invention propose a cart for an ultrasonic imaging system, said cart including a height adjustable column, and said column including an elevation device and a balancing unit adjustment device. Said elevator device is used for adjusting the height of said cart. Said balancing unit adjustment device includes a force balancing unit. Said force balancing unit includes an elastic assembly and said force balancing unit is used for balancing the lifting force required to achieve height adjustment by said elevator device.

Optionally, said column includes a base plate, a top plate, and a partition plate arranged adjacent to said top plate. A space is formed in-between said partition plate and said top plate and said elevation device is fixed between said base plate and said partition plate.

Optionally, said balancing unit adjustment device further includes a knob which is connected to said force balancing unit and is installed on the outside of said column for adjusting the elasticity of said elastic assembly, thereby altering said lifting force.

Optionally, said force balancing unit further includes an adjustment assembly which is provided in said space and connected to said knob. One end of said elastic assembly is fixed to the base plate and the other end is fixed to said adjustment assembly and said adjustment assembly is able to drive said elastic assembly to displace, thereby altering the elasticity thereof.

Optionally, said adjustment assembly includes a screw nut, a connection member, and a roller. One end of said screw nut is connected to said knob and is able to move in a first direction under the control of said knob, said first direction being perpendicular to the direction of rotation of said knob. Said connection member is connected to the other end of said screw nut. Said roller is fixed to said partition plate, and one end of said elastic assembly being fixed to said base plate, while the other end is fixed to said connection member by means of the roller.

Optionally, said adjustment assembly further includes a support frame which includes a body fixed to the top plate, and a plurality of extensions extending along the body toward the direction of said partition plate, and the plurality of extensions include through-holes respectively provided in said first direction, and said screw nut is installed along said plurality of through-holes.

Optionally, said screw nut includes a nut portion and a screw portion, and said nut portion is connected to said knob, and said screw portion is connected to said connection member.

Optionally, said elastic assembly is a tension spring.

Optionally, said elevation device includes a gas spring.

Optionally, the height adjustment of said cart is manually controlled.

Some embodiments of the present invention propose an ultrasonic imaging system, the ultrasonic imaging system including a height adjustable cart, said cart including an elevation device and a balancing unit adjustment device. Said elevator device is used for adjusting the height of said cart. Said balancing unit adjustment device includes a force balancing unit. Said force balancing unit includes an elastic assembly and said force balancing unit is used for balancing the lifting force required to by said elevator device to implement lifting.

Optionally, said cart includes a base plate, a top plate, and a partition plate arranged adjacent to said top plate. A space is formed in between said partition plate and said top plate and said elevation device is fixed between said base plate and said partition plate.

Optionally, said balancing unit adjustment device further includes a knob which is connected to said force balancing unit and installed on the outside of said cart for adjusting the elasticity of said elastic assembly, thereby altering said lifting force.

Optionally, said force balancing unit further includes an adjustment assembly which is provided in said space and connected to said knob. One end of said elastic assembly is fixed to the base plate and the other end is fixed to said adjustment assembly and said adjustment assembly is able to drive said elastic assembly to displace, thereby altering the elasticity thereof.

Optionally, said adjustment assembly includes a screw nut, a connection member, and a roller. One end of said screw nut is connected to said knob and is able to move in a first direction under the control of said knob, said first direction being perpendicular to the direction of rotation of said knob. Said connection member is connected to the other end of said screw nut. Said roller is fixed to said partition plate, and one end of said elastic assembly being fixed to said base plate, while the other end is fixed to said connection member by means of the roller.

Optionally, said adjustment assembly further includes a support frame which includes a body fixed to the top plate, and a plurality of extensions extending along the body toward the direction of said partition plate, and the plurality of extensions include through-holes respectively provided in said first direction, and said screw nut is installed along said plurality of through-holes.

Optionally, said screw nut includes a nut portion and a screw portion, and said nut portion is connected to said knob, and said screw portion is connected to said connection member.

Optionally, said elastic assembly is a tension spring.

Optionally, said elevation device includes a gas spring.

Optionally, the height adjustment of said cart is manually controlled.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A cart for an ultrasonic imaging system comprising a height adjustable column, and said column comprising:
   an elevation device which is used to adjust the height of said cart; and
   a balancing unit adjustment device, comprising a force balancing unit, said force balancing unit comprising an elastic assembly, wherein said force balancing unit is configured to balance the lifting force required to adjust a height of said column,
   wherein said column comprises a base plate, a top plate, and a partition plate provided adjacent to said top plate, wherein a space is formed between said partition plate and said top plate and said elevation device is fixed between said base plate and said partition plate.

2. The cart according to claim 1, wherein said balancing unit adjustment device further comprises a knob which is connected to said force balancing unit and is installed on the outside of said column for adjusting the elasticity of said elastic assembly to alter said lifting force.

3. The cart according to claim 2, wherein said force balancing unit further comprises:
   an adjustment assembly which is provided in said space and is connected to said knob, one end of said elastic assembly being fixed to the base plate and the other end being fixed to said adjustment assembly, wherein said adjustment assembly is configured to displace the elastic assembly in order to alter an elasticity of the elastic assembly.

4. The cart according to claim 3, wherein said adjustment assembly comprises:
   a screw nut, one end of which being connected to said knob and capable of moving in a first direction under the control of said knob, said first direction being perpendicular to the direction of rotation of said knob;
   a connection member which is connected to the other end of said screw nut; and
   a roller, said roller being fixed to said partition plate, and one end of said elastic assembly being fixed to said base plate while the other end is fixed to said connection member by means of the roller.

5. The cart according to claim 4, wherein said adjustment assembly further comprises:
   a support frame which comprises a body fixed to the top plate, and a plurality of extensions extending along the direction of the body toward said partition plate, and the plurality of extensions include through-holes respectively provided along said first direction, wherein said screw nut is installed along said plurality of through-holes.

6. The cart according to claim 4, wherein said screw nut comprises a nut portion and a screw portion, and wherein said nut portion is connected to said knob and said screw portion is connected to said connection member.

7. The cart according to claim 1, wherein said elastic assembly is a tension spring.

8. The cart according to claim 1, wherein said elevation device comprises a gas spring.

9. The cart according to claim 1, wherein the height adjustment of said cart is manually controlled.

10. An ultrasonic imaging system, comprising a cart, wherein the cart comprises a height adjustable column, said column comprising:
   an elevation device which is used to adjust the height of said cart; and
   a balancing unit adjustment device, comprising a force balancing unit, wherein said force balancing unit comprises an elastic assembly, and wherein said force balancing unit is configured to balance the lifting force required to adjust a height of said column,
   wherein said column comprises a base plate, a top plate, and a partition plate provided adjacent to said top plate, wherein a space is formed between said partition plate and said top plate and said elevation device is fixed between said base plate and said partition plate.

11. The ultrasonic imaging system of claim 10, wherein said balancing unit adjustment device further comprises a knob which is connected to said force balancing unit and is installed on the outside of said column for adjusting the elasticity of said elastic assembly to alter said lifting force.

12. The ultrasonic imaging system of claim 11, wherein said force balancing unit further comprises:
   an adjustment assembly which is provided in said space and is connected to said knob, one end of said elastic assembly being fixed to the base plate and the other end being fixed to said adjustment assembly, wherein said adjustment assembly is configured to displace the elastic assembly in order to alter an elasticity of the elastic assembly.

13. The ultrasonic imaging system of claim 12, wherein said adjustment assembly comprises:

a screw nut, one end of which is connected to said knob and capable of moving in a first direction under the control of said knob, said first direction being perpendicular to the direction of rotation of said knob;

a connection member which is connected to the other end of said screw nut; and a roller, said roller being fixed to said partition plate, and one end of said elastic assembly being fixed to said base plate while the other end is fixed to said connection member by means of the roller.

14. The ultrasonic imaging system of claim 13, wherein said adjustment assembly further comprises:

a support frame which comprises a body fixed to the top plate, and a plurality of extensions extending along the direction of the body toward said partition plate, and the plurality of extensions include through-holes respectively provided along said first direction, wherein said screw nut is installed along said plurality of through-holes.

15. The ultrasonic imaging system of claim 13, wherein said screw nut comprises a nut portion and a screw portion, and wherein said nut portion is connected to said knob and said screw portion is connected to said connection member.

16. The ultrasonic imaging system of claim 10, wherein said elastic assembly is a tension spring.

17. The ultrasonic imaging system of claim 10, wherein said elevation device comprises a gas spring.

18. The ultrasonic imaging system of claim 10, wherein the height adjustment of said cart is manually controlled.

* * * * *